United States Patent [19]

Frassica

[11] Patent Number: 5,601,537
[45] Date of Patent: Feb. 11, 1997

[54] CATHETER SYSTEM

[76] Inventor: James J. Frassica, 5 Essex Pl., Chelmsford, Mass. 01824

[21] Appl. No.: 463,194

[22] Filed: Jun. 5, 1995

[51] Int. Cl.$^6$ .................................................. A61M 5/00
[52] U.S. Cl. ........................ 604/264; 604/50; 604/280; 604/349; 604/95
[58] Field of Search ....................... 604/22, 43–45, 604/50–53, 93, 264, 280–283, 274, 316, 317, 318, 328, 349, 95; 606/159, 167, 170, 171, 180; 128/772

[56] References Cited

U.S. PATENT DOCUMENTS

| | | |
|---|---|---|
| 207,932 | 9/1878 | Alvord . |
| 761,235 | 5/1904 | Kepler . |
| 1,644,919 | 10/1927 | Hayes . |
| 2,173,527 | 9/1939 | Agayoff .................................. 128/349 |
| 2,896,629 | 7/1959 | Warr ...................................... 128/349 |
| 4,445,509 | 5/1984 | Auth ...................................... 128/305 |
| 4,762,130 | 8/1988 | Fogarty et al. ....................... 128/348.1 |
| 4,834,724 | 5/1989 | Geiss et al. ............................ 604/280 |
| 4,950,232 | 8/1990 | Ruzicka et al. ........................ 604/43 |
| 4,955,859 | 9/1990 | Zilber ...................................... 604/8 |
| 5,009,643 | 4/1991 | Reich et al. .......................... 604/165 |
| 5,059,169 | 10/1991 | Zilber ...................................... 604/8 |
| 5,087,252 | 2/1992 | Denard ................................. 604/346 |
| 5,129,910 | 7/1992 | Phan et al. ........................... 606/127 |
| 5,246,445 | 9/1993 | Yachia et al. ........................ 606/108 |
| 5,308,354 | 5/1994 | Zacca et al. .......................... 606/159 |
| 5,334,211 | 8/1994 | Shiber ................................... 606/159 |

OTHER PUBLICATIONS

"Anatomy, Descriptive & Surgical" by Henry Gray 1977 Crown Publishers pp. 98–1001, 1004–1007, 1026–1027.
"Ancient Inventions", 1st Ed 1994 by Peter James & Nick Thorpe Ballantine Books pp. 15 & 16.
"Perspectives in Urology" pp. 117–134 Hoffman–Larducue Pub of American Urological Assoc 1976.
"Antique Medical Instruments" pp. 74–75 by C. Keith Wilbur, M.D. Schiffer Pub. Ltd.
"Urology Products" Bard Urological Div. 6 pages Product Data Sheets.
"A Presentation of Catheters and Urological Specialties for . . . " 1 page Foley Catheters/Urological Specialties.
Exhibit A: Baird Specialty Procedure Trays.

*Primary Examiner*—V. Millin
*Assistant Examiner*—N. Kent Gring
*Attorney, Agent, or Firm*—Vernon C. Maine

[57] ABSTRACT

Apparatus and methodology for applying catheters, dilators and occluders to mammalian genito-urinary and gastro-intestinal passages, using rotational manipulation of threaded or helically-formed catheters and threaded dilators and occluders. Threaded or helical catheters are inserted into the opening of the selected passage far enough to engage a thread segment, the other end of the catheter is then manually rotated to draw the catheter into the passage. Threaded dilators and occluders are similarly applied.

16 Claims, 6 Drawing Sheets

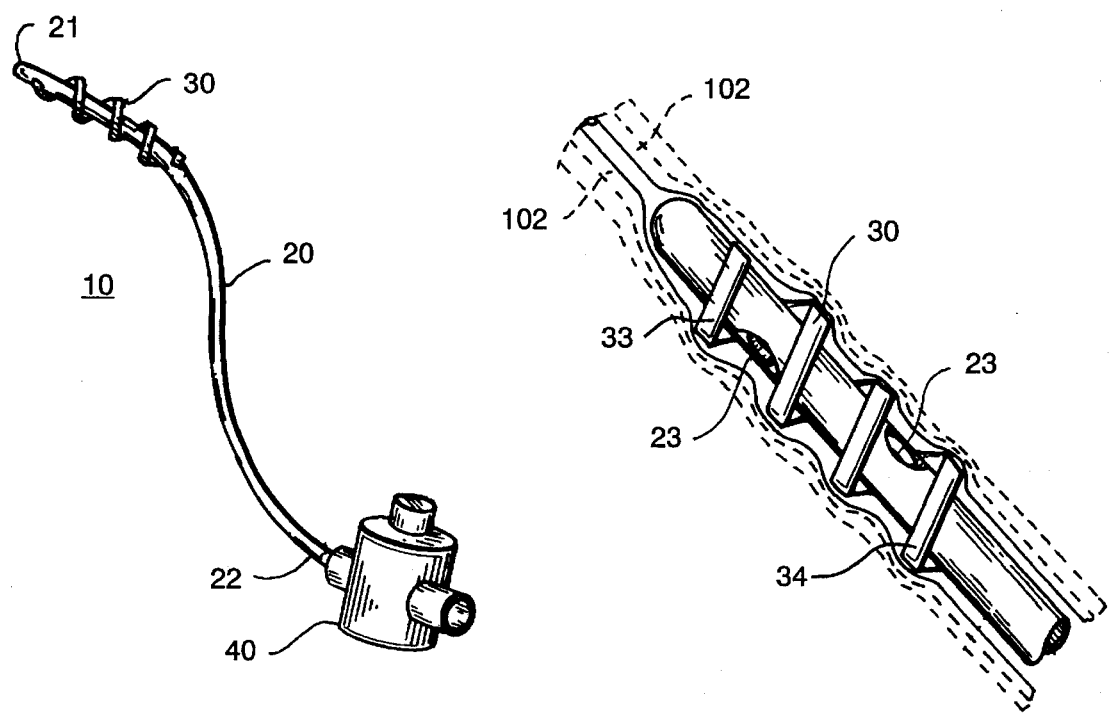
FIG. 1
FIG. 3
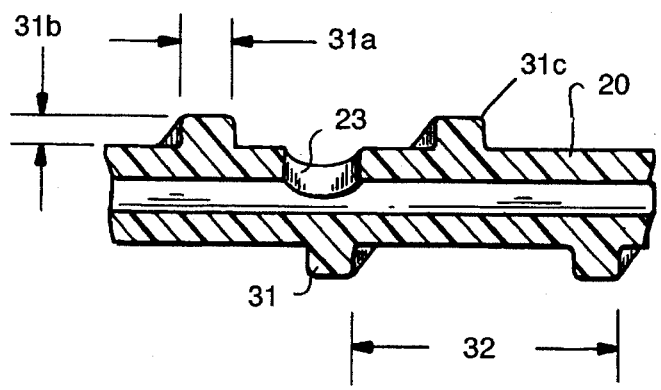
FIG. 2

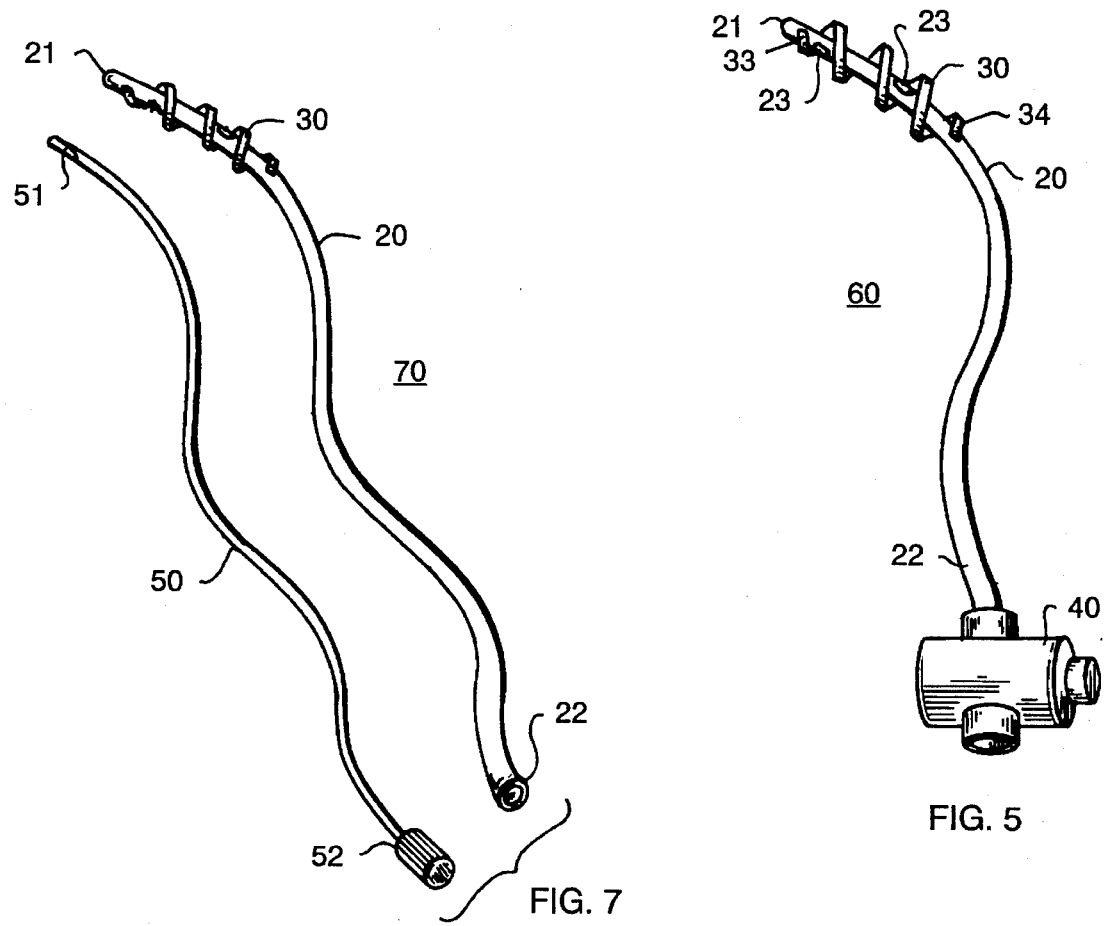
FIG. 7
FIG. 5
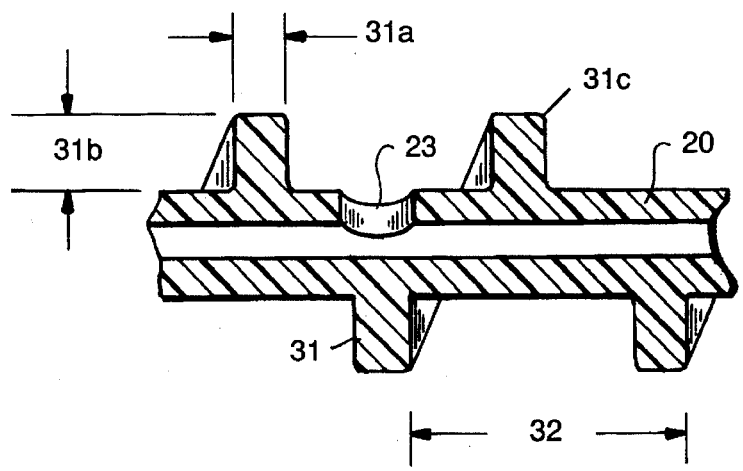
FIG. 6

CATHETER SYSTEM

BACKGROUND OF THE INVENTION

1. Technical Field of the Invention

This invention most generally relates to the apparatus and methods of catheterization and related treatments of the genito-urinary and gastro-intestinal passages of mammals.

More particularly, the invention relates to a screw-based means of applying catheters, dilators and occluders to mammalian genito-urinary and gastro-intestinal passages.

2. Background Art

Urinary outlet problems most likely have been around for as long as humans.

The present state of the treatment of such problems leaves much to be desired. Intermittent catheterization must be done four to six times a day or more to service a normal rate of urine accumulation in the bladder. This repeated bodily invasion poses a high risk of infection. Patients who are determined to retain a normal degree of mobility must carry a spare catheter and cleaning supplies. They must be confident of finding greater privacy, better facilities and more time to attend to this function than non-affected persons.

The anatomy of the adult male urinary tract, as illustrated in FIG. 4, has a bladder 104 where urine is collected prior to exiting the body via the urethra 106. The bladder 104 converges into the urethra 106 at a muscular exit called the bladder neck 105. The first approximately one inch of the urethra lies within the prostate gland 107. The next approximately half inch passes through the sphincter 108, which is the muscular flow valve that controls the release of urine. The remaining six inches of the urethra lie in a spongy zone, exiting the body at the meatus 109.

The catheters of the prior art are large and stiff, difficult and uncomfortable to administer, and uncomfortable to wear for extended periods. The technique of pushing a catheter into the urethral passage requires an alternate pushing, waiting, and retracting slightly and renewing the push if the catheter is causing too much discomfort or spasmic reaction. There is a degree of skill, tolerance and patience required that takes much time, training and practice to learn. Also, long term catheterization can result in encrustation of the catheter in the bodily passage.

The difficulty, discomfort, risk of injury and infection, inhibition and inconvenience of the methods and tools of the known art results in the deprivation for many patients of the freedom to work, play and travel as do unaffected people.

History has the ancient Chinese using onion stalks to relieve people of acute urinary retention. Literature refers to such problems as far back as 206 B.C., more than 2000 years ago.

Romans used catheters, first invented by Erasistratus, a Greek doctor in the third century B.C. Roman catheters were fine tubes made of bronze. The Roman gynecologist Soranus describes how catheters could be used to push stones out of the way and back into the cavity of the bladder, and thus restore urine flow.

Excavations in Pompeii unearthed several bronze catheters. These instruments were well constructed but relatively simple and showed that designs changed little from the period 79 AD until 1700 A.D.

However, during the 17th and 18th centuries catheter construction became more complex with an intensified search for an appropriate substance that would be at once flexible, non-irritating and functional.

England, France, and the U.S.A. had individuals and companies deeply involved with urinary catheters during this period. Many variations were produced but they all caused much stress on the patient when these rigid devices were pushed into the urethra. The first practical breakthrough was by the French using gum elastic catheters—a catheter that would bend better in the urethral channel and not scour the mucosa so much in the process.

Charles Goodyear improved upon what the French produced when he successfully vulcanized crude rubber. The problem of manufacturing an instrument which was both sufficiently rigid to enable it to be pushed through the urethra into the bladder and yet flexible enough to negotiate the path, had at last reached the point of practicality, not withstanding its shortcomings.

At that time, and still to this day, a functional urethral catheter is defined as one that is flexible enough to negotiate the bends and stable enough to push through the length of the urethral passage.

The tradition use and continuing contemporary acceptance of push-to-advance catheterization may be attributed in part to the interior wall of the urethra being a series of longitudinal folds running the length of the urethra, effectively obscuring alternative means for placing the catheter.

The French urologist J. J. Cazenave, with the hopes that his country would regain leadership in the catheter field, dedicated 25–30 years of his life improving the flexible durable catheter. This was in the late 1800's and his catheter, made of decalcified ivory, was a dated device but shows the consistency of the state of the art wherein catheters are pushed into and negotiated along the urethral passage toward the bladder.

During the past 300 years or so, intensified development efforts were stimulated by professional pride, national pride and financial rewards. These efforts yielded many improvements, such as changes to size, curve shape, materials of construction, smoothness, lubricants, coatings, combinations of materials, physical properties, chemical properties and more, yet all subscribed to the basic principle of external push-to-advance.

The normal process of emptying the bladder can be interrupted by two causes. One is bladder outlet obstruction and the other is failure of the nerves linking the bladder to the brain. The most frequent cause of bladder outlet obstruction in males is enlargement of the prostate gland by hypertrophy or hyperplasia.

The prostate is a chestnut-sized gland lying inferior to the bladder and surrounding approximately the fist inch of the urethra. In older males, it is not uncommon for a progressive enlargement of the prostate to constrict the prostate urethra. This condition, known as benign prostatic hyperplasia (BPH), can cause a variety of obstructive symptoms, including urinary hesitancy, straining to void, decreased size and force of the urinary stream and in extreme cases, complete urinary retention possibly leading to renal failure.

Females, and males with no benign prostatic hyperplasia condition, might also have the inability to empty their bladder because of the nerves linking the bladder to the brain. This condition is known as neuropathic bladder, may occur in a wide variety of conditions which include spina bifida, multiple sclerosis, spinal injury, slipped disc and diabetes.

A number of irritative symptoms may also be experienced with urinary incontinence, including urinary frequency, discomfort and humiliating accidents.

Efforts to treat retention-with-overflow incontinence fall into general categories of surgical and catheterization.

Outlet obstructions resulting from BPH and Prostatic hypertropy are commonly treated by a surgical procedure known as transurethal resection. The procedure is painful, recovery is long, (about 1 year), and success is uncertain (less than 80%).

When other problems prevent the bladder from emptying effectively, catheterization is usually a solution. The two common catheterization methods are continuous and intermittent.

During continuous catheterization an indwelling catheter is retained in the bladder by a water filled balloon. It drains urine continuously from the bladder via a connecting tube into a bag which is attached to the leg or bed. The bag has a tap so that the urine can be emptied at intervals. The catheter is usually inserted by a doctor or nurse and changed about every four to six weeks.

During intermittent catheterization a simple catheter made of plastic, rubber, or metal is inserted by the patient or a helper for just long enough to empty the bladder completely, which is typically about one minute. Most patients learn to catheterize themselves and thereby gain a large degree of independence. This process is repeated about every 3–4 hours during the day and occasionally as needed at night.

In most mammals, mucous membranes line all those passages by which the internal parts communicate with the exterior, and are continuous with the skin at the various orifices of the surface of the body. They are soft and velvety, and very vascular, and their surface is coated over by their secretion, mucus, which is of a tenacious consistence, and serves to protect them from the foreign substances introduced into the body with which they are brought in contact.

They are described as lining the two tracts—the genito-urinary and the gastro-intestinal; and all, or almost all, mucous membranes may be classed as belonging to and continuous with the one or the other of these tracts. Catheterization of any of these similar bodily passages may at times be useful or necessary.

With the exception of balloon catheters, the current art of dilators has also changed little over the passage of time. A shaft with an increasing taper, bulbus structure, or enlarged end is pushed from without the passage to advance the tool through the restricted passage, thus forcing by longitudinally-applied pressure the lateral expansion of the passage walls. This push-to-advance method necessitates a stiff shaft which has all the same liabilities as traditional catheters. Catheters inherently provide a degree of this dilatorial function to the extent that the passage is opened sufficiently to accommodate the catheter.

Occluders of the prior art are similar instruments with similar liabilities; basically a bulb or plug on a shaft is inserted within a passage to provide blockage, or driven all the way into the bladder and allowed to seat as a plug at the neck of the urethra to prevent the flow of fluid from the bladder.

In summary, there are problems in making present push-in catheters stiff enough for penetration and flexible enough to make the turns without undue risk of trauma to the wall of the passageway when being pushed in; and once installed, comfortable enough to wear for an extended period. Self-administration is inhibited by all of the short-comings of the present art, and further injury, infection and discomfort may result from the resulting improper self-care.

The long history of push-in urinary catheters and the longitudinal folds of the walls of the urethra and ureter have fostered a here-to-for untested assumption that any other approach would somehow be unworkable and possibly damage or scour the mucosa further, or otherwise cause pain or distress to the subject. The soft, moist, pliant wall quite simply does not suggest a capability for providing a longitudinal grip on a threaded or helical device while allowing the sliding passage of the threads without incurring damage, but rather suggests or leads back to the traditional push-in tools and methodology.

SUMMARY OF THE INVENTION

It is among the principal objects of the invention to improve the apparatus and methodology of catheterization, dilatation and occlusion of genito-urinary and gastro-intestinal passages of humans and other mammals, to provide an alternative to the traditional push-in methodology of such treatments, to reduce trauma and risk of damage caused by the tradition devices and methods for such treatments, to reduce the inhibition associated with and facilitate self-catheterization for patients for both intermittent and long-term purposes, and to extend such capability to patients with less manual dexterity.

It is an object of the invention to provide a screw-based means for rotational advancement of a catheter, dilator or occluder into a genito-urinary or gastro-intestinal passage whereby the subject device is substantially drawn into the passage by the longitudinal grip and pull of a screw or helix element on the walls of the passage as the lower end or outboard end of the device is rotated.

It is another object to provide increased resistance to twisting over the length of the tube or shaft in order to effectively transmit rotational or torsional forces from the lower end to the screw or helix element of the system or device, while keeping resistance to bending of the tube or shaft of the system or device to a minimum in order to facilitate negotiation of the turns of the passage as well as promote the comfort of the patient during the insertion and the period of treatment.

It is yet another object to include in a catheter of the invention means for collecting fluids that emulate or accumulate at a position that is intermediate to the desired placement of the upper end or tip of the catheter in the passage.

It is still yet another object to provide a removable means for insertion such as an application tool which can be removed when the catheter is in place, that allows for use of a less rigid catheter tube.

It is an additional object to delineate the basic methodology by which the invention may be practiced.

Still other objects and advantages of the present invention will become readily apparent to those skilled in this art from the following detailed description, wherein I have shown and described preferred and other embodiments of the invention, simply by way of illustration of the best mode contemplated by me on carrying out my invention. As will be realized, the invention is capable of other and different embodiments, and its several details are capable of modifications in various obvious respects, all without departing from the invention.

BRIEF DESCRIPTION OF THE DRAWINGS

FIG. 1 is a perspective view of one embodiment of the invention, a threaded catheter for a male.

FIG. 2 is a cross sectional view of the threaded portion of the catheter of FIG. 1.

FIG. 3 is a illustration of the threaded end of the catheter of FIG. 1 engaged in the urethra.

FIG. 5 is a perspective view of another embodiment of the invention, a threaded catheter for a female.

FIG. 6 is a cross sectional view of the threaded portion of the threaded catheter of FIG. 5.

FIG. 7 is a perspective view of yet another embodiment of the invention; a threaded catheter which is inserted with the aid of a flexible shaft stylet.

DESCRIPTION OF THE PREFERRED EMBODIMENT

Figure 4:
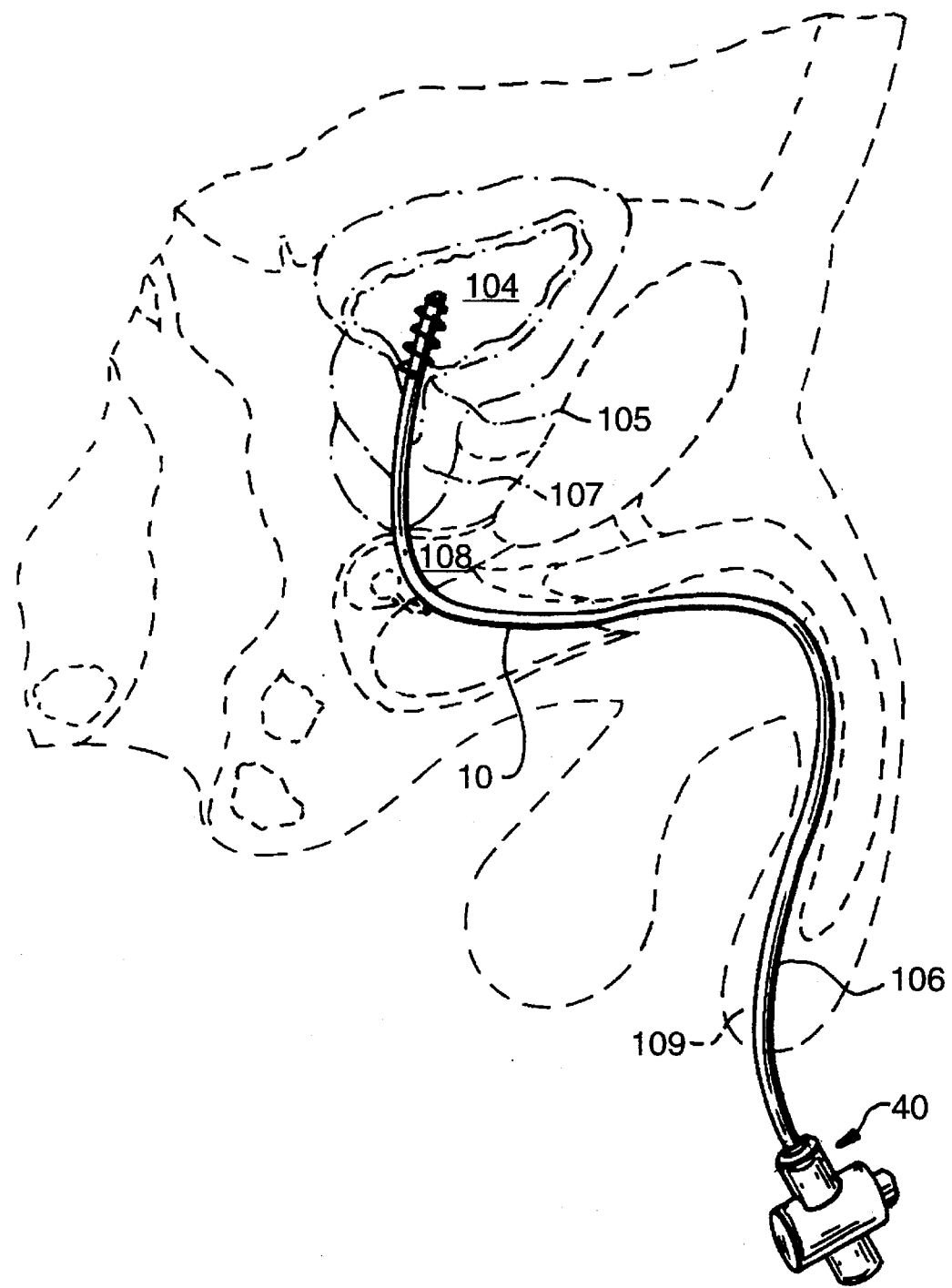
FIG. 4 is a front elevation illustration of the abdominal anatomy of a typical male subject; the catheter of FIG. 1 shown fully emplaced in the urethra with the threaded portion extending into the bladder.

To those skilled in the art, the invention admits of many variations and appellations in apparatus and methodology.

By way of example, there is provided in accordance with the present invention, a screw-based means for advancing a catheter, dilator or occluder into mammalian genito-urinary or gastro-intestinal passages such as the urethra or ureter, for the usual purposes associated with such devices where no incising or rupture of passage walls or membranes is intended. Placement may be for a few minutes up to several weeks, depending on the condition and the requirements of the patient.

As another example, a catheter tube will have one or more ports for collecting fluid on the upper end, which connect with one or more lumens that run the length of the tube and discharge the fluid at the lower end. Additionally, in accordance with one aspect of the invention, the tube will have an external thread or thread segment at the upper end. The leading or upper end of the thread, and the lower end as well, are tapered to zero height so that the thread can advance or retract with a gradual engagement and displacement of the wall of the passage.

The upper end tip is manually inserted into the opening of the passage far enough to at least partially engage the thread within the passage. Then with manual rotation of the tube or shaft, the head of the catheter is literally screwed into the passage, drawing the length of the catheter tube with it. As the tube progresses, it requires sufficient torsional strength over its length so that the force of the manual rotation at the lower end of the tube is effectively transmitted to the screw threads at the upper end of the tube. Rotating the catheter in one direction causes it to advance, and in the opposite direction causes it to retract.

This and other embodiments of the catheter may be connected to a means for flow control, such as a normally-closed push button valve that allows the user to simply void or drain into a toilet or urinal, or into a container intended for the purpose.

As still yet another example, a tube or shaft may be constructed of a composite of polymer and reinforcing fibers, or other materials, designed to provide increased resistance to twisting so that manual rotation is most effective, and decreased resistance to bending so that the discomfort of application through the winding passage and necessary movement during extended placements, is minimized.

As an additional example, the catheter tube may have an additional lumen connected to a series of secondary sideports located an intermediate length on the tube, and draining at the lower end of the tube.

As another additional example, a catheter system in accordance with another aspect of the invention, uses a catheter tube with external threads and a non-rotational fitment in the lumen near the upper end of the tube, and uses a flexible shaft stylet as an application tool. The stylet is inserted into the lumen through the lower end of the tube, and the tip of the stylet is configured to mate with the fitment so that when the grip on the bottom stylet is rotated, the torsional force is transmitted through the tip and fitment to the external threads of the catheter.

The stylet can rotate the catheter in either direction to advance or retract the catheter, and simply be pulled out when the catheter is in place. The stylet thus provides the necessary torsional strength to apply or install the catheter, and permits the catheter tube wall to be therefor smaller and more flexible.

As yet another additional example, the catheter tube, or at least the upper end of the tube, may be formed as a helix rather than having external threads. Being applied in the same fashion as the threaded catheter, the coils or turns of the helix provide the longitudinal grip on the walls of the passage for advancing and retracting the catheter. The tube, in this instance, would have sufficient torsional strength over its length so that manual rotation of the lower end of the tube advances and retracts the catheter. The upper end or tip of the helical tube catheter may terminate in a bulb. As a variation on this example, the catheter may incorporate a soft, flexible mandrel which functions as the bulbous tip and provides internal support to the coils of the helix.

As still yet another additional example, a stylet incorporating a helix may be used as an application tool to insert a simple catheter; the stylet providing both the screw-based means in the form of the helix, and the necessary stiffness and torsional strength to turn the helix for insertion, and then being removed so that the flexible catheter can function normally.

As a further example the invention may be practiced in one aspect by the method of using a catheter system with a screw-based means for advancing a catheter through a genito-urinary or gastro-intestinal passage with or without a stylet or other application tool, inserting the tip of the catheter into the opening of the selected passage, aligning the tip with axis of the entrance to the passage, advancing the tip into the passage until the screw-based means, which may be an external thread segment or a helix, is at least partially engaged in the entrance to the passage, then rotating the screw-based means so as to draw the head of the catheter into the passage.

As another further example, a dilator in accordance with the invention, for use in genito-urinary and gastro-intestinal passages, has a flexible shaft incorporating a tapered bulb, with a least one external thread segment, and is administered in the same fashion as threaded catheters of the invention.

As yet another further example, an occluder for genito-urinary and gastro-intestinal passages is constructed similarly to a dilator of the invention, except that there would be no thread segment at the midpoint, or point of largest diameter of the bulb, so that the blocking or plug function of the occluder is uniformly applied to the walls of the passage.

As still yet another further example, an occluder may have one thread segment disposed above the midpoint of the bulb and another thread segment disposed below the midpoint of the bulb, to facilitate advancing and retracting the occluder.

Referring now to FIG. 1, catheter 10 for males is made up of tube 20 with thread 30, attachable to flow control device 40. Tube 20 is extruded from polyurethane material, has an inside diameter of 0.06 inches, an outside diameter of 0.125 inches, and is approximately 13 inches long. The durometer as measured on the smooth, outside wall of the tube is 85 Shore A. Upper end 21 is closed off, and the tip is rounded to a uniform radius of about 0.06 inches. Lower end 22 of tube 20 is simply cut off square and attached to flow control device 40. Tube 20 is sufficiently strong such that when the majority of its length is contained within the urethra, it will withstand and transmit torque as applied by finger force at the lower end external of the urethra, to the helix.

Referring to FIGS. 1 and 2, thread 30 is formed from a strip of polyurethane material with a rectangular cross section 31 of width 31a of 0.05 inches and height 31b of 0.032 inches, attached to tube 20 starting 0.2 inches from upper end 21 and extending four complete turns around tube 20 in a clockwise direction towards lower end 22 at a uniform pitch 32 of 0.25 inches, resulting in a four-turn helix about one inch long. It is readily apparent from FIGS. 1 and 2 that the thread height 31b of catheter 10 at 0.032 inches, is greater than twenty percent (20%) of the 0.125 inches of the outside diameter of the catheter tube, in order to expand and penetrate the longitudial folds of the urethra sufficiently to achieve a useful grip by the thread.

The diameter of the helix formed by thread 30 of catheter 10 is equal to the sum of twice the thread height 31b and the outside diameter of catheter 10, or in this case 2 times 0.032 inches plus 0.125 inches or approximately 0.19 inches. The circumference of the helix formed by thread 30 is calculated as $\pi$ (pi) times the diameter, or in this case 3.14 times 0.19 or approximately 0.6 inches. The ratio of the pitch of thread 30 of catheter 10, at 0.25 inches, to the circumference of the helix it forms, at 0.6 inches, is less than 1 to 1, thereby improving the leverage of the screw thread for converting rotation into longitudinal pulling power as compared to larger ratios. The shoulders 31c of threads 30 have a radius of 0.015 inches. In small quantities, thread 30 may be attached to tube 20 by wicking tetrahydrofuran (THF) solvent under the thread using a fine hollow tube. Catheter 10 may be molded in large quantities with thread 30 being an integral part of the molded structure.

Referring to FIG. 3, two sideports 23, are oval in shape, the major axis of the oval parallel with the axis of tube 20, and being about 1.5 times the minor axis, which is about equal to the diameter of the lumen or passageway of the catheter. The two sideports are configured 180 degrees apart radially, and spaced longitudinally to fit between the turns of the helix.

Referring to FIG. 3, the upper end 33 of thread 30 is tapered from zero to full height in one-half turn of the helix, to facilitate gentle, gradual displacement of urethra wall 102 by thread 30 when catheter 10 is rotated clockwise for forward motion into the urethra. Lower end 34 of thread 30 is similarly tapered to facilitate counterclockwise rotation of catheter 10 for removal from the urethra. The difference between width 31a and pitch 32 shown in FIG. 2 is sufficient that the urethra wall does not bridge between adjacent turns, but rather is only displaced in a manner closely conforming to the cross section of the thread 30, thereby providing the longitudinal grip on urethra wall 102 for advancing and retracting the helix.

Referring to FIG. 4, the catheter 10 is shown in proper position for draining bladder 104, after it has been advanced through the urethra until the helix passes out of the urethra into the bladder.

It is apparent from the anatomy shown in FIG. 4, that threads 30 must be limited in length to be advanced to any point above the spincter 108, so that the spincter may contract directly onto the smooth, round, exterior of tube 20, thereby preventing leakage around the tube and further constraining the catheter from migrating or being forced out of the urethra by pressure from urine in the bladder. It is apparent from the drawing that there is a limit to the length of thread 30 on a catheter that can be advanced to a position above the spincter 108, not more than about six turns within the optimal range of pitch, and still fit within the bladder 104 without interference. A limited length of thread 30 also localizes the area of pulling force to the upper end of the catheter, assuring that the entire length of the catheter is drawn, not pushed, through the passage.

Referring to FIG. 5, the catheter 60 for females, similar to catheter 10 for males, is made up of tube 20 with thread 30, attachable to flow control device 40. Tube 20 is extruded from polyurethane material, has an inside diameter of 0.063 inches, an outside diameter of 0.125 inches, and is approximately seven inches long. The durometer as measured on the smooth, outside wall of the tube is 85 shore a. Upper end 21 is closed off, and the tip is rounded to a uniform radius of about 0.06 inches. Lower end 22 of tube 20 is simply cut off square and attached to flow control device 40. Tube 20 is sufficiently strong such that when the majority of its length is contained within the urethra, it will withstand and transmit torque as applied by finger force at the lower end external of the urethra, to the helix.

Referring to FIGS. 5 and 6, thread 30 of catheter 60 is formed from a strip of polyurethane material with a rectangular cross section 31 of width 31a of 0.05 inches and height 31b of 0.10 inches, attached to tube 20 starting 0.2 inches from upper end 21 and extending four turns around tube 20 in a clockwise direction towards lower end 22 at a uniform pitch 32 of 0.25 inches, resulting in a four-turn helix about one inch long. It is readily apparent from FIGS. 5 and 6 that the thread height 31b of catheter 60 at 0.10 inches, is much greater than twenty percent (20%) of the 0.125 inches of the outside diameter of the catheter tube, in order to expand and penetrate the longitudial folds of the female urethra sufficiently far to achieve a useful grip by the thread.

The diameter of the helix formed by thread 30 of catheter 60 is equal to the sum of twice the thread height 31b and the outside diameter of catheter 60, or in this case 2 times 0.10 plus 0.125 or approximately 0.33 inches. The circumference of the helix formed by thread 30 is calculated as π (pi) times the diameter, or in this case 3.14 times 0.33 or approximately 1.0 inches. The ratio of the pitch of thread 30 of catheter 60, at 0.25 inches, to the circumference of the helix it forms, at 1.0 inches, is much less than 1 to 1, thereby improving the leverage of the screw thread for converting rotation into longitudinal pulling power as compared to larger ratios. The shoulders 31c of threads 30 have a radius of 0.015 inches. In small quantities, thread 30 may be attached to tube 20 by wicking tetrahydrofuran (THF) solvent under the thread using a fine hollow tube. Catheter 60 may be molded in large quantities with thread 30 being an integral part of the molded structure.

Referring to FIG. 5, two sideports 23, are oval in shape, the major axis of the oval parallel with the axis of tube 20, and being about 1.5 times the minor axis, which is about equal to the diameter of the lumen or passageway of the catheter. The two sideports 23 are configured 180 degrees apart radially, and spaced longitudinally to fit between the turns of the helix.

Referring to FIG. 5 and 6, the upper end 33 of thread 30 is tapered from zero to full height in three-quarter turn of the helix, to facilitate gentle, gradual displacement of urethra wall by the thread when catheter 60 is rotated clockwise for forward motion into the urethra. Lower end 34 of thread 30 is similarly tapered to facilitate counterclockwise rotation of catheter 60 for removal from the urethra. The difference between width 31a and pitch 32 is sufficient that the urethra wall does not bridge between adjacent turns, but rather is displaced in a manner closely conforming to cross section 31 of thread 30, thereby providing the longitudinal grip on the urethra wall for advancing and retracting the helix, similar to catheter 10 of FIG. 3.

Catheter 60 of FIG. 5 is in proper position for draining the bladder after it has been advanced through the urethra until the helix passes out of the urethra into the bladder, similar to catheter 10 of FIG. 3, but for females.

A detailed method of self-administration of catheters 10 and 60 is explained:

The user assembles materials including a catheter in a sterile package, container for urine, soap and water, if the catheter is not pre-lubricated then water soluble lubricant, mirror (for females), and tissues. The user will then wash hands and urethral opening with soap and water, remove catheter from sterile package, squeeze out small amount of lubricant into clean tissue, dip the upper end tip of the catheter into the lubricant, and manually engage the catheter into the urethral opening, (the mirror may be helpful for females to assist in locating the opening).

The user will then gently push the tip of the catheter in far enough to engage the thread with the urethra, and gently rotate the tube of the catheter in the direction of the helix or thread, preferably clockwise, to advance the catheter into the urethra, until a stream of urine appears in the tube. The user should then pause to drain the bladder, directing the urine into the container, then resume rotation of the catheter until it is no longer advanced by the rotation, indicating that the helix has passed into the bladder and the catheter is in proper position.

The user then applies the flow control devise to the lower end of the catheter and empties the bladder periodically as required. The catheter is removed when appropriate using similar precautions for cleanliness and containment, by rotating the catheter in a direction opposite the direction of insertion, presumably counterclockwise.

Figure 8:
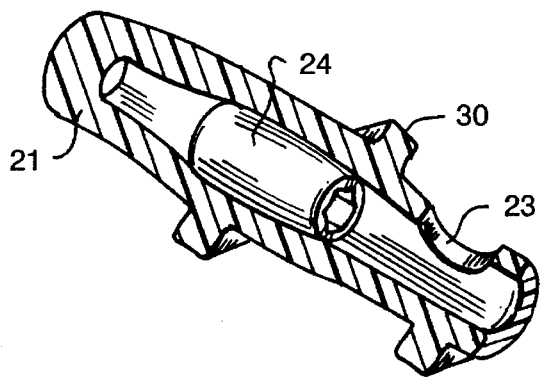
FIG. 8 is a cross section of the tip of the catheter of FIG. 7, showing the non-rotational fitment that receives the tip of the stylet of FIG. 9.
Figure 9:
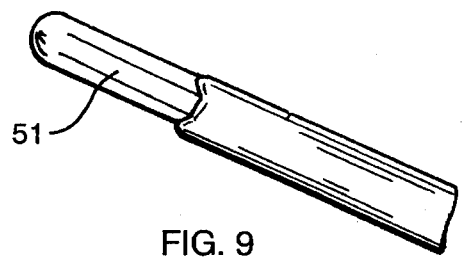
FIG. 9 is a perspective view of the tip of the flexible shaft stylet of FIG. 7 that is inserted into the fitment of FIG. 8.

Referring to FIGS. 7, 8 and 9, another embodiment contemplated by the claims is illustrated by catheter 70, which is made up of tube 20 with thread 30 applied in the form of a helix, and utilizing flexible shaft stylet 50 as an insertion and retraction tool. Stylet 50 has grip 52 at the lower end, for turning. Tube 20 is configured with non-rotational fitment 24 near upper end 21 so that stylet 50 can be inserted through lower end 22, up through the center of tube 20, and tip 51 of stylet 50 be then engaged with fitment 24 in a manner that allows rotation of grip 52 in one direction to rotate catheter 70 and advance thread 30 into the urethra, and in the other direction to retract thread 30 through the urethra.

The flexible shaft of stylet 50 is sufficiently strong such that when it is fully inserted into the catheter, it will withstand and transmit torque as applied by finger force at the lower end knurled knob grip 52 external of the urethra, to the thread 30 helix. Stylet 50 is removed after the catheter is installed, and reinserted for retracting the catheter.

Fitment 24 is an elongated collar with a multi-faceted interior wall, securely anchored within tube 20, and configured to receive in a non-rotational relationship the insertion of tip 51. Tip 51 is configured with a corresponding elongated, multi-faceted exterior shape, and rounded end, to readily enter fitment 24 when gently urged with forward and rotational pressure.

Figure 10:
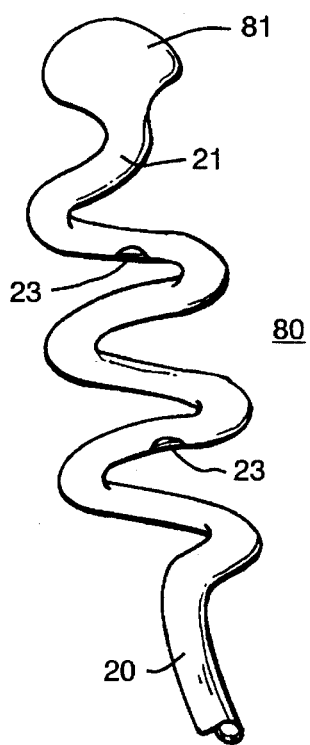
FIG. 10 is a perspective view of still yet another embodiment of the invention, a catheter with the upper or forward end formed as a helix.

Referring to FIG. 10, another embodiment contemplated by the claims is illustrated by catheter 80, similar to catheters 10 and 60, except that at least a portion of tube 20 near upper end 21 is formed in the shape of a uniform spiral, or helix, creating the functional equivalent of thread 30, upper end 21 terminating in bulb 81, this embodiment being administered in the same manner as catheters 10 and 60.

Figure 11:
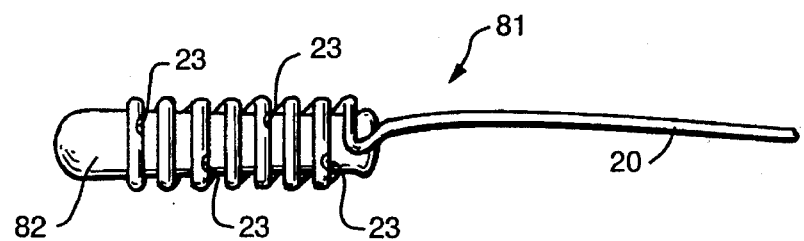
FIG. 11 is a perspective view of an additional embodiment of the invention; a helical tube catheter with a flexible mandrel supporting the coils of the helix.

Referring to FIG. 11, another embodiment contemplated by the claims is illustrated by catheter 81, similar to catheter 80 except that a soft, flexible mandrel 82 is provided to provide a guiding tip and internal support to the helical section of tube 20. This embodiment is administered in the same manner as other catheters of the invention.

Figure 12:
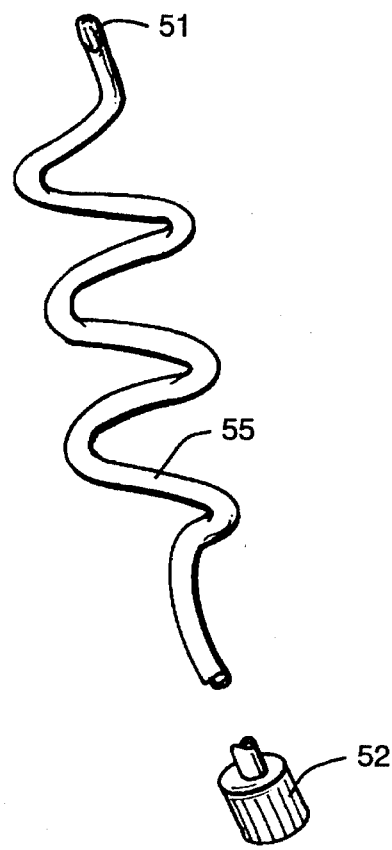
FIG. 12 is a perspective view of an additional embodiment of the invention; a helical stylet used to install a simple tube catheter.

Referring to FIG. 12, another embodiment contemplated by the claims is a non-threaded catheter, similar in appearance to conventional push-in catheters, but which includes upper fitment 24 of FIG. 8, and utilizes helical stylet 55, with tip 51 of FIG. 9, as an insertion and retraction tool.

Figure 13:
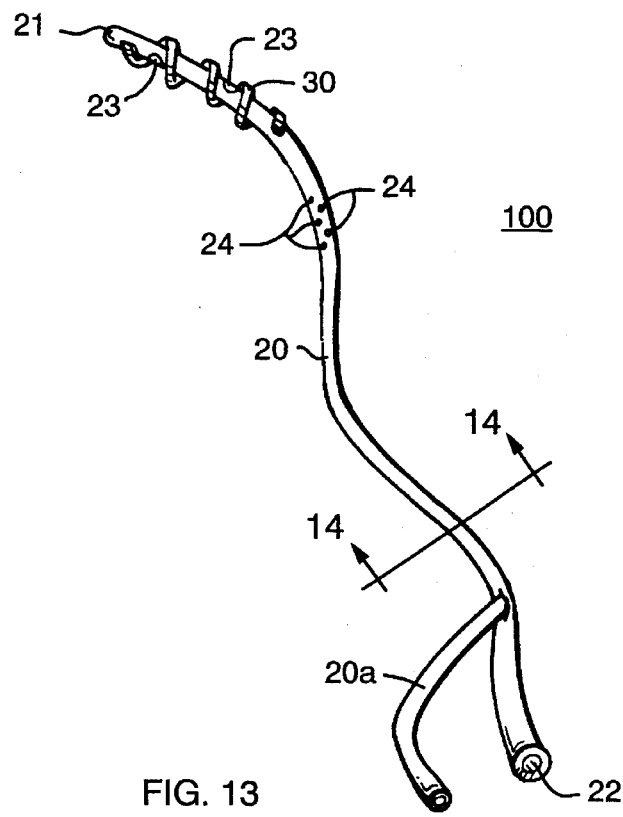
FIG. 13 is a perspective view of another additional embodiment of the invention; a threaded catheter with two coaxially configured tubes or lumens, the outer lumen communicating with sideports at an intermediate length on the catheter, the center lumen communicating with the sideports near the tip or upper end of the catheter.
Figure 14:
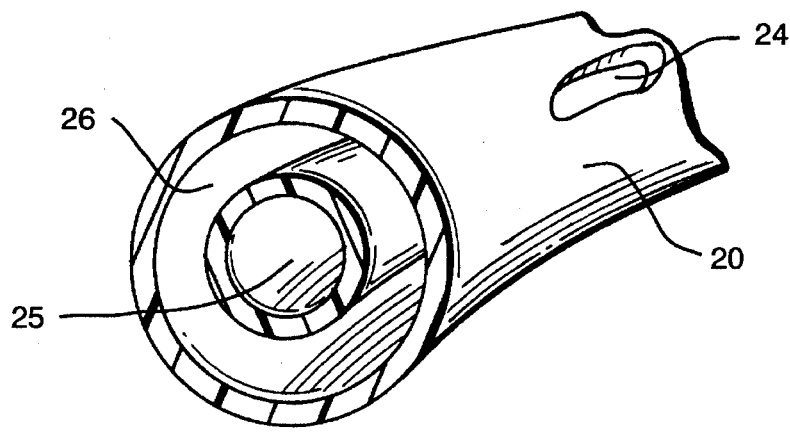
FIG. 14 is a cross sectional view of the embodiment of FIG. 12, illustrating the co-axial configuration of the two lumen.

Referring to FIGS. 13 and 14, another embodiment contemplated by the claims is illustrated by multiple-lumen catheter 100, similar in appearance to catheter 10 of FIG. 1, but having a tube 20a within tube 20 in a coaxial configuration where center lumen 25 is communicating with sideports 23 near the upper end 21 of tube 20 to drain urine, and outer lumen 26 is communicating with secondary sideports 24 located at an intermediate length on tube 20, to drain fluids emulating from within the urethral channel, as may occur incidental to surgery or other urethral trauma. Tube 20a extends through the sidewall of tube 20 near lower end 22, to facilitate collection of the respective fluids.

Figure 15:
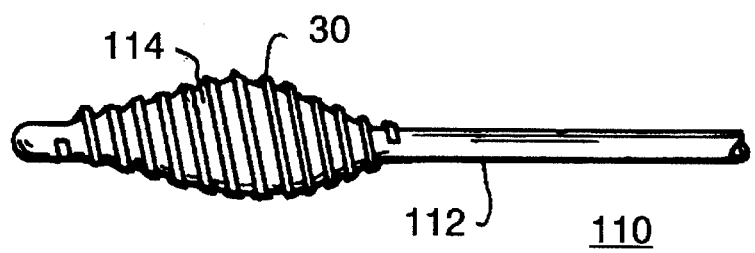
FIG. 15 is a side elevation of a dilator in accordance with one aspect of the invention.
Figure 16:
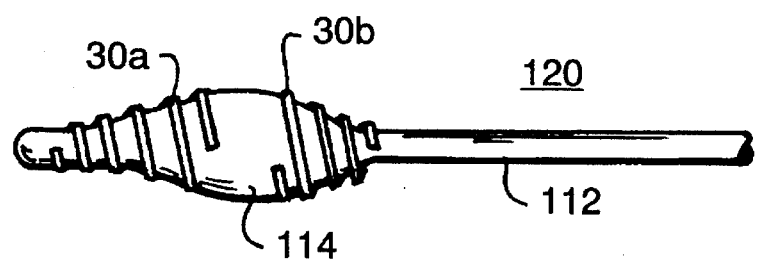
FIG. 16 is a side elevation of an occluder in accordance with one aspect of the invention.
Figure 17:
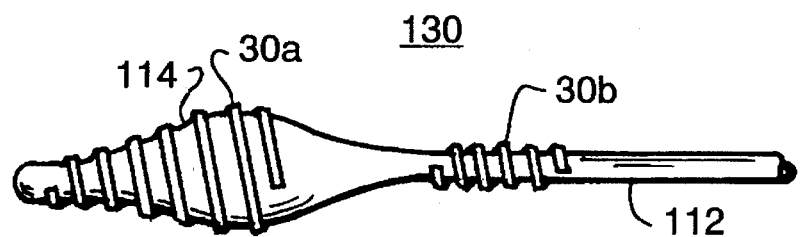
FIG. 17 is a side elevation of an occluder in accordance with another aspect of the invention.

Referring now to FIGS. 15, 16 and 17, dilator 110 and occluder 120 and 130 are similarly constructed by configuring the upper end of a flexible shaft 112 with tapered bulb 114, and disposing thereon threads similar to threads 30 on catheter 10 of FIGS. 1 and 2. The ends of thread 30 are tapered for ease of advancing and retracting, again similar to catheter 10 of FIGS. 1 and 2.

Dilator 110 and occluder 120 and 130 are likewise similarly applied to urethral and similar bodily passages, for their respective benefits.

Occluder 120 is distinguished from dilator 110 in that thread 30 is divided into an upper and lower thread segments 30a and 30b, and likewise tapered at their abutting ends so that there is no thread height at the midpoint of tapered bulb 114, thereby providing a non-threaded section to effectively plug the passage once occluder 120 is properly positioned.

Occuluder 130 is distintuished from occluder 120 principly in that thread segment 30b of occluder 130 is disposed on the shaft 112 below bulb 114 thereby providing a non-threaded proximal or lower end to bulb 14 which is most effective when positioned at the bladder neck of the urethra.

In summary, the method and apparatus of the disclosed screw-in catheter system, and related screw-in dilator and occluder, is a radical departure from thousands of years of prior art of push-in urethral catheters and offers significant advantages in ease of application, safety and wearing comfort over the catheters of the known art. It will enhance the convenience, comfort and control of patients, particularly self-administering patients, enabling a broader range of self-administering users to enjoy greater freedom and mobility, and reducing the incidence of injury and infection relating to the shortcomings of the prior art. It is further adaptable to other genito-urinary and gastro-intestinal body passages with similar characteristics.

The objects and advantages of the invention may be further realized and attained by means of the instrumentalities and combinations particularly pointed out in the appended claims. Accordingly, the drawings and description are to be regarded as illustrative in nature, and not as restrictive.

I claim:

1. A catheter for catheterizing mammalian genito-urinary and gastro-intestinal passages, said catheter comprising a flexible catheter tube having a lower end and an upper end and a lumen communicating there between, said upper end of said tube configured with an external screw thread of uniform pitch, said thread having a thread height of at least one fifth (⅕) of the outside diameter of said catheter tube and a thread pitch not greater than the circumference of said thread.

2. The catheter system of claim 1, said thread extending no more than six turns in length.

3. The catheter of claim 1, said thread height tapering at each end of said thread from full height to no height.

4. The catheter of claim 1, said lower end of said catheter tube being attachable to a means for flow control.

5. The catheter of claim 1, said catheter tube having a side port, said lumen communicating with said side port.

6. The catheter of claim 1, said catheter tube constructed of a composite of polymer and reinforcing fibers.

7. The catheter of claim 1, said catheter tube configured to accept insertion of a flexible shaft stylet through said lower end into said lumen, the tip of said stylet engagable in a non-rotational fitment secured in said lumen near said upper end of said catheter tube.

8. A method for catheterizing a mammalian genito-urinary or gastro-intestinal passage comprising the steps of:

utilizing a flexible catheter having an upper end and a lower end and a lumen communicating there between, said catheter configured with an external screw thread of uniform pitch at said upper end, said thread having a thread height of at least one fifth (⅕) of the outside diameter of said catheter and a thread pitch not greater than the circumference of said thread, introducing the tip of said catheter into an opening to said passage, aligning said tip with said passage, advancing said tip into said passage with a combination of rotational and forward pressure until said thread is engaged one turn into said passage, rotating said catheter thereby advancing said catheter into position within said passage.

9. The method of claim 8, said thread extending no more than six turns in length.

10. The method of claim 9, said passage being the urethra of a male subject, said position being where said thread of said catheter is above the sphincter of said subject whereby said sphincter may contract around said catheter tube at a point below said thread.

11. The method of claim 10, said lower end of said catheter tube being attachable to a means for flow control.

12. The method of claim 8, said thread height tapering at each end of said thread from full height to no height.

13. The method of claim 8, said catheter tube having a side port and a lumen, said lumen communicating between said side port and said lower end of said tube.

14. The catheter of claim 8, said catheter tube constructed of a composite of polymer and reinforcing fibers.

15. The method of claim 8, said catheter tube configured to accept insertion of a flexible shaft stylet through said lower end into said lumen, the tip of said stylet engagable in a non-rotational fitment secured in said lumen near said upper end of said catheter tube, said rotating of said catheter preceeded by the following steps:

inserting said stylet through said lower end of said catheter into said lumen, advancing said stylet through said lumen into engagement with said non-rotational fitment, said rotating of said catheter comprising rotating of said stylet while engaged therewith.

16. A catheter for catheterizing mammalian genito-urinary passages, said catheter comprising a flexible catheter tube having a lower end and an upper end and a lumen communicating there between, said upper end of said tube configured with an external screw thread of uniform pitch, said thread having a thread height of at least one fifth (⅕) of the outside diameter of said catheter tube and a thread pitch not greater than the circumference of said thread.

* * * * *